United States Patent [19]
Amidon et al.

[11] Patent Number: 5,674,530
[45] Date of Patent: Oct. 7, 1997

[54] METHOD FOR MAKING A MULTI-STAGE DRUG DELIVERY SYSTEM

[75] Inventors: Gordon L. Amidon; John R. Crison, both of Ann Arbor, Mich.

[73] Assignee: Port Systems, L.L.C., Ann Arbor, Mich.

[21] Appl. No.: 383,830

[22] Filed: Feb. 6, 1995

Related U.S. Application Data

[63] Continuation-in-part of Ser. No. 251,731, May 31, 1994, Pat. No. 5,387,421, which is a continuation of Ser. No. 826,253, Jan. 27, 1992, abandoned, which is a continuation of Ser. No. 648,968, Jan. 31, 1991, abandoned.

[51] Int. Cl.$^6$ ............................................. A61K 9/22
[52] U.S. Cl. .................. 424/472; 424/453; 424/464; 424/466; 424/468; 424/470
[58] Field of Search ........................... 424/464, 451, 424/453, 466, 468, 470, 472

[56] References Cited

U.S. PATENT DOCUMENTS

| | | | |
|---|---|---|---|
| 4,773,907 | 9/1988 | Urquhart et al. | 424/467 |
| 4,777,049 | 10/1988 | Magruder et al. | 424/457 |
| 4,783,337 | 11/1988 | Wong et al. | 424/468 |
| 4,865,849 | 9/1989 | Conte et al. | 424/466 |

OTHER PUBLICATIONS

Gennaro, A.R. (1985). Remington's Pharmaceutical Sciences. Mack Pub. Co., pp. 1625–1630 and 1638–1643.

*Primary Examiner*—Raj Bawa
*Attorney, Agent, or Firm*—Kohn & Associates

[57] ABSTRACT

A method of making a drug delivery system (10) includes the steps of filling a first water permeable capsule half with a drug and an osmotic agent and plugging an open-end (24) of the capsule (12). The method further includes the steps of disposing a water permeable film (30) over the capsule (12) and plug (28), filling a second capsule half (14) with a drug (18), and releasably mounting an open end (34) of the second capsule half (14) over the plugged end (24) of the first capsule half (12).

5 Claims, 7 Drawing Sheets

*Fig - 12* NUMBER OF COATS APPLIED

*Fig - 13*

METHOD FOR MAKING A MULTI-STAGE DRUG DELIVERY SYSTEM

This application is a continuation-in-part of U.S. Pat. No. 08/251,731, filed May 31, 1994, now U.S. Pat. No. 5,387,421, which is a continuation of U.S. Ser. No. 07/826,253, filed Jan. 27, 1992, now abandoned, which is a continuation of U.S. Ser. No. 07/648,968, filed Jan. 31, 1991, now abandoned.

TECHNICAL FIELD

This invention relates generally to drug delivery systems.

BACKGROUND OF THE INVENTION

It has been recognized that there is a need for a drug delivery system which yields an increase in the oral dosing interval of drugs exhibiting presystemic loss metabolism while simultaneously maintaining bioavailability equivalent to the immediate release dosage form. Such drugs would otherwise either require short interval dosing, such as periodic oral dosing having short periods between each oral dosing.

Various drug delivery systems, commonly referred to as time released systems, have attempted to solve this problem by continuously releasing amounts of the drug throughout the travel of the drug through the digestive track. For example, the U.S. Pat. No. 4,773,907 to Urquhart et al, issued Sep. 27, 1988, discloses a delivery system comprising a capsule containing dosage forms comprising a semipermeable wall surrounding a compartment containing drug. A passageway through the semipermeable wall releases drug from the dosage form to the environment. The U.S. Pat. No. 4,777,049 to Magruder et al, issued Oct. 11, 1988, discloses an osmotic delivery system. The system provides a device including a wall which can be a laminate comprising a semipermeable lamina and lamina arrangement with a microporous lamina. The lamina provides micropaths for emitting external fluid into the osmotic device. The device includes an opening having an erodible element, such as a gelatin plug that erodes and forms an osmotic passageway in the environment of use. Within the device is a modulating agent in nonequilibrium proportions. Upon the influx of fluid into the device, there is co-solubilization of a useful agent which is then released from the device. Thusly, co-solubilization of a modulating agent and a useful agent controls the release of the useful agent and results in the delayed release of the useful agent resulting from a reduction of the concentration of the modulating agent. This results in an osmotic system and a method of preprogramming to a desired time of release, a delayed release or a delayed pulsed release of agent. However, the delayed pulse of release is over a base line release and not a true pulse release from a zero base line.

The U.S. Pat. No. 4,783,337 to Wong et al, issued Nov. 8, 1988, discloses an osmotic system comprising a wall which is at least in part a semipermeable material that surrounds a compartment. An osmotic composition, or several osmotic compositions are contained within the compartment defined by the wall and a passageway in the wall connects the first composition with the exterior of the system. The first composition causes imbibition of fluid which results in the delivery of the suspension or solution through the aforementioned passageway. This can end up being a multi-chamber device.

The aforementioned patents do not result in a truly pulsatile release. Pulsatile release, as used herein, implies an initial first release followed by a period of time where there is absolutely no release. Then, after the predetermined period, there is a true pulse release. Unlike prior art systems, it is desirable to provide a drug delivery system for non-linear presystemic loss drugs which will release fractions of the total dose at specified sites and time in the gastro-intestinal track so that bioavailability will not be compromised by the decreased release rate of conventionally controlled or sustained release dosage forms.

There are several advantages to a true pulsatile delivery system in extending the dosing interval. For those drugs which are first pass metabolized, an increase in delivery rate to the portal system results in a decrease in metabolism. For those drugs exhibiting non-linear prehepatic metabolism a larger fraction of drug will escape metabolism and therefore be available. For those drugs with incomplete absorption due to low permeability, poor solubility or in which case the absorption rate limited by rate of dissolution, enhancers can be added to increase the bioavailability. The pulse time and release rate can be programmed to match the immediate release dosage form profile. The pulse time and release rate from pulsatile delivery can be more reproducible than the immediate release dosage form which relies on patient compliance and rate of gastric emptying for input of drug to the site of absorption, that being the small intestine. The result is a decreased variability in plasma level time curves. The clinical efficacy of a pulsatile delivery system can be established to provide equivalent bioavailability to the conventional dosage form. Accordingly, patient compliance is increased through the use of a reduced and/or simpler dosing schedule. The pharmacodynamics of the pulsatile system can be made to match the established immediate release dosage. Thereby, the metabolic rates equivalent to that obtained from an approved dosing schedule can be obtained, hence no unusual accumulation of metabolites or altered metabolic profile results. The pulse delay and amount being pulsed are programmable to a variety of dosing schedules such that allowance for circadian rhythms is possible in order to optimize the pharmacodynamic response throughout the day. Finally, the optimal dosing schedule for two or more drugs, tailored to their individual pharmacokinetic and pharmacodynamic properties, can be optimized using this technology. The present invention provides an improved means of providing a pulsed dose or doses which are capable of providing all of the aforementioned advantages.

SUMMARY OF THE INVENTION

In accordance with the present invention, there is provided a method of making a drug delivery system includes the steps of filling a first capsule half with a drug and an osmotic agent, the capsule being water permeable. The method further includes the step of plugging an open-end of the capsule, disposing a water permeable film over the capsule and plug, filling a second capsule half with a drug, and releasably mounting an open end of the second capsule half over the plugged end of the first capsule half.

FIGURES IN THE DRAWINGS

Other advantages of the present invention will be readily appreciated as the same becomes better understood by reference to the following detailed description when considered in connection with the accompanying drawings wherein:

FIGS. 9A and B are chromatograms from blank samples and actual samples from dog studies discussed below;

DETAILED DESCRIPTION OF THE INVENTION

A drug delivery system constructed in accordance with the present invention is generally shown at 10 in the Figures. This system generally includes a first container in the form of a capsule half 12 and a second container in the form of a mating capsule half 14. The first capsule half 12 includes an inner chamber 16 for containing a drug 18 therein. Of course, the shape of and size of the capsule half can be varied in accordance with the art.

Figures 1A, 1B, 2:
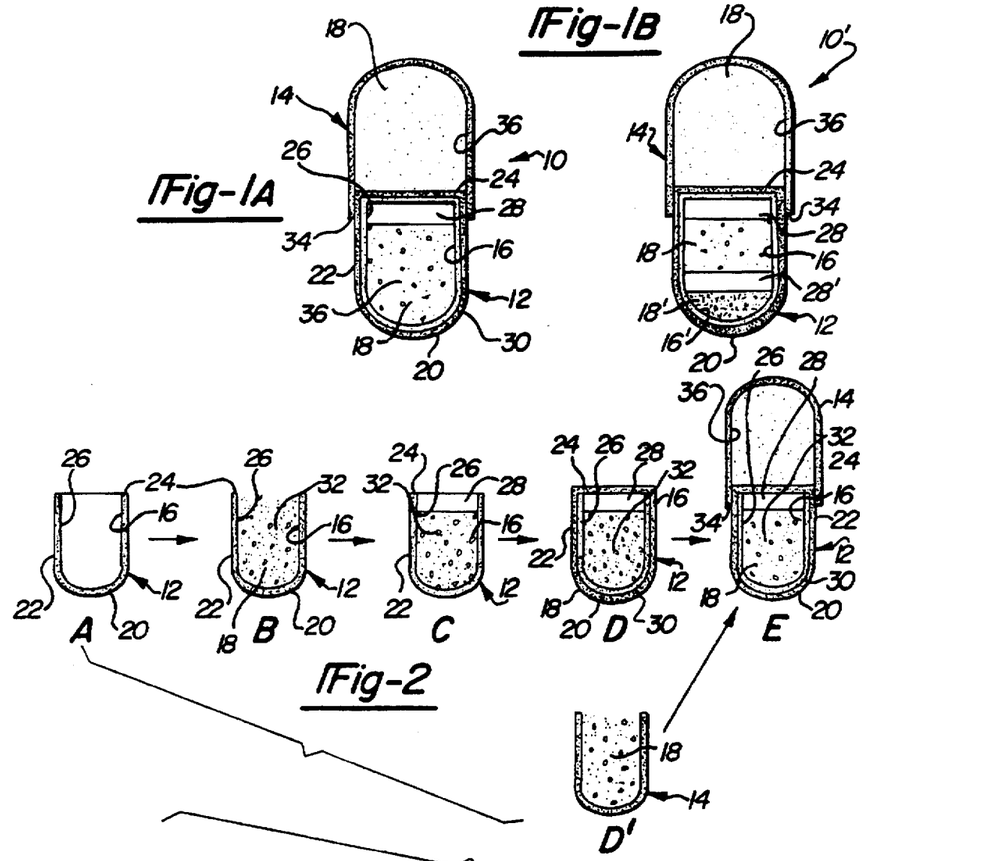
FIG. 1A is cross sectional view of a drug delivery system made in accordance with the present invention.
FIG. 1B is a cross sectional view of a multi-chamber drug delivery system made in accordance with the present invention.
FIG. 2 shows the steps of manufacturing the drug delivery system of the present invention.

More specifically referring to FIG. 1A, the first capsule half 12 includes a closed end portion 20 extending to a substantially annular wall 22 defining a second open end 24. The wall 22 and opening 24 define an internal passageway 26 opening to the external environment thereof. A plug 28 is disposed in the passageway 26 for plugging the opening 24 closed. The plug 28 is releasable from the opening 24 upon the application of pressure from within the inner chamber 16. The invention is characterized by the first capsule 12 including a mechanism reactive with the external environment for increasing the pressure within the inner chamber 16 and forcing the plug 28 out of the passageway 26 to release the drug 18 from the inner chamber 16 and out of the passageway 26.

As shown in FIG. 1B, the system can include multiple chambers 16,16' and multiple plugs 28,28'. Each chamber 16,16' includes a mechanism reactive with the external environment for first forcing out plug 28 to release the contents of chamber 16 and then sequentially force out the second plug 28' to release the contents of chamber 16'.

With more specific regard to the reactive mechanism, the reactive mechanism can be a pumping mechanism, such as an osmotic means for pumping fluid through the wall of the first capsule half 12 increasing the internal pressure within the inner chamber 16. Accordingly, once the drug delivery system 10 is ingested at a predetermined time, the reactive mechanism will cause a release of the drug 18 from the first capsule half 16 at predetermined time after ingestion. The rate of internal pressure increase results in the release, timing of the rate being controlled by means described below.

For example, to create the osmotic pump of the present invention, the first capsule half 12 includes a membrane film 30 disposed thereover and over the plug 28 for allowing fluid to pass into the inner chamber 16 as a result of an osmotic pressure gradient therethrough. The osmotic pump further includes an osmotic agent 32 disposed within the inner chamber 16 for creating an osmotic pressure gradient across the membrane film 30 and capsule wall when disposed in the fluid of the external environment.

The open end 34 of the second substantially cupped shaped capsule 14 is seated over and in mating engagement with the open end 24 of the first capsule half 12. The second capsule half 14 includes an inner chamber 36 containing drug 18 therein. The second capsule half 14 is releasably connected to the first capsule half 12 so as to release upon ingestion of the capsule thereby providing an immediate release of drug 18 followed after a predetermined time by the pulse release of the drug 18 from the second capsule half 12.

The capsule halves 12,14 can be made from various materials, preferably water containing gelatins.

The plug 28 can be made from various materials which can, in a plug shape, form a friction fit within the passageway 26 of the first capsule half 12. Examples of plug materials are bees' wax and synthetic bees' wax, carnauba wax, partial glycerides and polyethylene glycol (PEG), fatty esters, glyceryl stearate, palmitosterate, paraffin wax, and white wax.

Various osmotic agents can be used with the present invention. Agents such as lactose, sorbitol and mannitol can be used. Optionally, the drug contained within the capsule halves 12,14 may also provide sufficient osmotic pressure thereby obviating the need of an additional osmotic agent.

Further the reactive mechanism can be achieved by other agents. For example, swellable gels can be used. Examples of these agents are acrylic acid polymers, hydroxypropyl methyl cellulose, and ethyl cellulose. Alternatively, gas producing agents can be used, such as sodium bicarbonate. It is possible that these agents or additional agents can be added which effect the environment during release. For example, acidifying agents can be added which would acidify a well defined intestinal area where the pulsed dose is released thereby potentiating absorption of the drug without effecting the remainder of the system. Time release systems cannot achieve this localized effect as the agent would be released throughout the tract and substantially diluted.

Various film materials can be used for forming the membrane film 30. Examples of composition for forming the film materials are cellulose acetate (all grades), cellulose acetate butyrate (all grades), cellulose acetate phthalate (all grades), and combinations of the above. Also, ethylcellulose can be used.

Table 1 provides a listing of sixty-six drugs which could be used in accordance with the present invention, the list not being an all-inclusive list of such list but rather examples of such drugs.

FIG. 2 schematically illustrates the method of making the drug delivery system 10 in accordance with the present invention. Step A in FIG. 2 shows the first capsule half 12 being empty. Step B shows the capsule half being filled with osmotic reagent 32 and drug 18. As stated above, the drug 18 per se could be the osmotic agent. As shown in Step C, the open end 24 of the first capsule half 12 is plugged with the plug member 28. Step D shows the water permeable film 30 being disposed over the capsule 12 and plug 28. Step D' shows the filling of the second capsule half 14 with the drug 18. Finally, Step E shows the mounting of the open end 34 of the second capsule half 14 over the plugged end 24 of the first capsule half 12.

Of course, many of the steps shown in FIG. 2 can be accomplished by various filling, plugging, and coating methods. For example, Table 2 shows the composition of a preferred captopril containing capsule made in accordance with the present invention. The capsule was made by the following specific method. Also, multi-chambered systems can be made by repeating the filling and coating steps.

Weighed citric acid, anhydrous, USP, was disposed in a mortar and ground thoroughly to a fine powder. Anhydrous lactose, USP, microcrystalline cellulose, NF, sorbitol, NF, Croscarmellos sodium, NF, were added to the mortar containing the citric acid, anhydrous, USP and mixed well. The captopril, USP was added to the mortar containing the excipients of the previous step and mixed thoroughly. The magnesium stearate, BP was added to the mortar and stirred gently. Homogeneity of the mixture was checked from three spots in the mortar taking one gram sample. A 98.4% yield was obtained.

A number zero hard gelatin two piece capsule was filled with 350 mg±1.5 mg of the fill mix or adjusted to give a potency of 67 mg based on the assay result from the previous step. Utilizing the ingredients set forth in Table 2, a plurality of capsules were filled.

Gelucire 50/02 was melted using a water bath to a constant temperature of 60° C.±5° C. 120 mg of the melted gelucire 50/20±20 mg was filled into each capsule or five drops of the Gelucire was dispensed using a transfer pipette into each capsule. The capsules were allowed to sit until the gelucire sufficiently solidified. The specific weight (amount) of Gelucire or other plug material can be varied. The capsules were weighed and then placed in a six inch diameter coating pan. Rotation of the coating pan was started and adjusted to a speed of 30 rpm±5 rpm. Using a Sigma Glass Spray Unit, the bottle was filled with 225 ml±25 ml coating solution. A spray top was fitted on the bottle and tightly capped. A suitable spray pattern was obtained using a compressed air unit by adjusting the air flow and the capsules were sprayed in the pan for sixty seconds. The capsules were allowed to turn in the pan with a stream of compressed air blowing into the pan for sixty seconds. The weight gain of the capsules was calculated as follows:

$$\% \text{ gain} = \frac{\text{coated weight} - \text{uncoated weight}}{\text{uncoated weight} \times 100}$$

Thusly, when referring to coating thickness, percent coat is referenced, that meaning the percent gain in weight of the capsule coated by the membrane film. The greater the percent gain, the thicker the coating on the capsule.

To make the final capsules, 66 mg±1 mg of the captopril immediate release blend (50%) was disposed into the cap of the size number zero hard gelatin and mounted onto the capsule previously referred to above. The cap was placed on the body taking care not to lose any of the material in the cap or to disrupt the coating on the capsule body. These fine finished capsules were stored in polyethylene bags until tested as described below.

In a preferred embodiment of the present invention, the water permeable film 30 is disposed over the capsule 12 and plug 28 by dipping or immersing the capsule 12 and plug 28 in a reservoir or tank containing the film material. That is, the capsule 12 and plug 28 are immersed in a bath of film material in order to dispose the water permeable film 30 over the capsule 12 and plug 28. The dipping method of the present invention can be performed either prior to filling of the capsule or after the capsule has been filled.

Application of the permeable film 30 by dipping or immersion of the capsule 12 into the film material reduced one of the major problems associated with spray coating which is volatilization of flammable solvents such as acetone. Since spray coating can aerosolize the solvent, it creates a potential for fire or explosion. By immersing the capsule 12 and plug 28 in order to dispose the coating 30 about the capsule 12 and plug 28, much less solvent is aerosolized and, thus, the risk of fire or explosion is reduced. Additionally, since much less solvent is required for dip coating than for spray coating, the dipping or immersion method is much less expensive than spray coating.

The coating material is dissolved in a suitable solvent in order to obtain the desired concentration of the coating to be applied to the capsule 12. Generally, the concentration of the coating material ranges from approximately one to five percent by weight (w/v) of solvent. The preferred range being approximately two to four percent by weight (w/v) of solvent.

Suitable solvents for use in dip coating or immersion coating of the capsules 12 include acetone for water insoluble materials and water (H₂O) for water soluble coating materials. Other suitable solvents known to those skilled in the art can also be used.

The capsules 12 are dip coated at approximately room temperature (~20° C.). Following the application of the water permeable film by the dip coating method of the present invention, the coated capsules are dried or "cured" by subjecting the coated capsules to a temperature ranging from approximately 20° C to 60°C. The preferred drying temperature being approximately 20° C. or room temperature. The coated capsules are subjected to drying temperatures for between one minute to twenty-four hours or until the capsules have reached suitable dryness.

Thickness of the permeable film 30 applied to the capsule can be varied by either increasing/decreasing the number of coats applied or by varying the concentration of the film material to be applied to the capsule 12 and plug 28.

Figure 4:
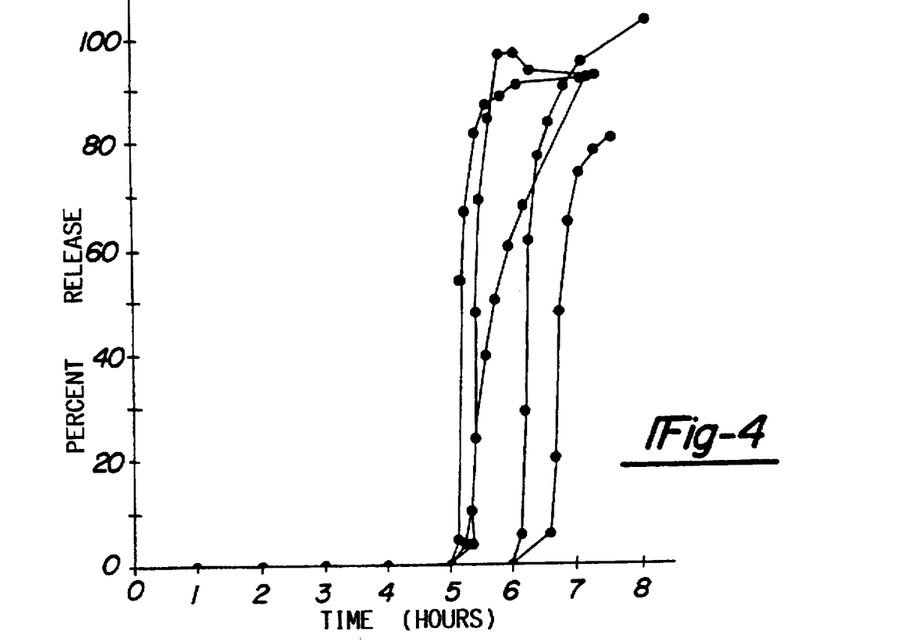
FIG. 4 is a graph showing the percent release of drug from drug delivery systems made in accordance with the present invention over time.

FIG. 4 shows the effective ability of the capsules made in accordance with the present invention to generate a pulse release. First capsule halves 12 made in accordance with the method previously described were tested in vitro for ability to create an osmotic pressure therein to force the release of the plug member 23 and thereby release captopril therefrom. The method consisted of the steps of disposing capsule halves coated as previously described in 28 ml of pH 6.5 buffer solution at 37° C. Samples were initially taken once every hour. At the five hour time period, samples were taken every ten minutes.

A number zero hard gelatin two piece capsule (Capsugel, Greenwood, S.C.) was filled with 200 mg of the osmotic charge (sorbitol/lactose)-aspirin formulation. Gelucire 50/02 was melted using a water bath to a temperature of 50°–60° C. The Gelucire 50/20 was added into each capsule or five drops of the Gelucire was dispensed using a transfer pipette into each capsule. The capsules were allowed to sit until the Gelucire sufficiently solidified. The specific weight (amount) of Gelucire or other plug material can be varied. The capsules were weighed and then dip coated (immersed)

in an acetone solution containing 0.7% w/v triacetin (Sigma Chemical Co., St. Louis, Mo.) and 2.1% cellulose acetate (FMC Corp., Philadelphia, Pa.). The capsules were allowed to air dry between coats. The weight gain of the capsules was calculated as previously described above. Thusly, when referring to coating thickness, percent coat is referenced, that meaning the percent gain in weight of the capsule coated by the membrane film. The greater the percent gain, the thickener the coating on the capsule.

Capsules having several different numbers of coated layers 30 applied by dipping or immersing the capsule in coating material, as previously described above, were placed in a USP Paddle Dissolution Apparatus (Vankel) containing 900 ml of Simulated Intestinal Fluid, USP (pH 7.5) at 37° C. and rotated at 100 r.p.m. Samples were taken at different time intervals and the total aspirin released at each time point was determined using UV-HPLC and spectrophotometric methods well known in the art. The results of these release studies are illustrated in Table V, FIG. 12, and FIG. 13.

Figure 12:
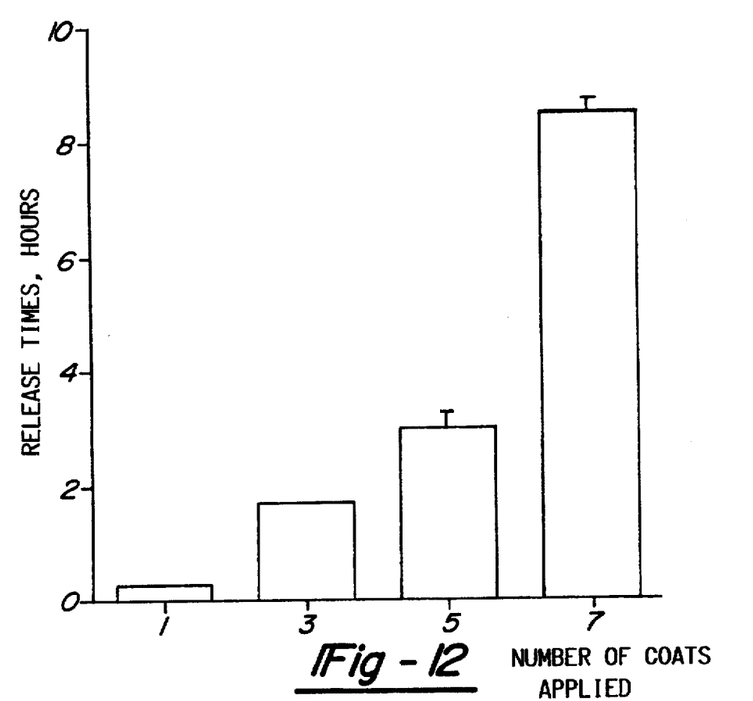
FIG. 12 is a graph showing the release times of drug as a function of the number of coatings applied to the delivery system.

FIG. 12 illustrates the correlation between the number of cellulose film coats and the release time of aspirin in the Simulated Intestinal Fluid at pH 7.5 at 37° C.

Figure 13:
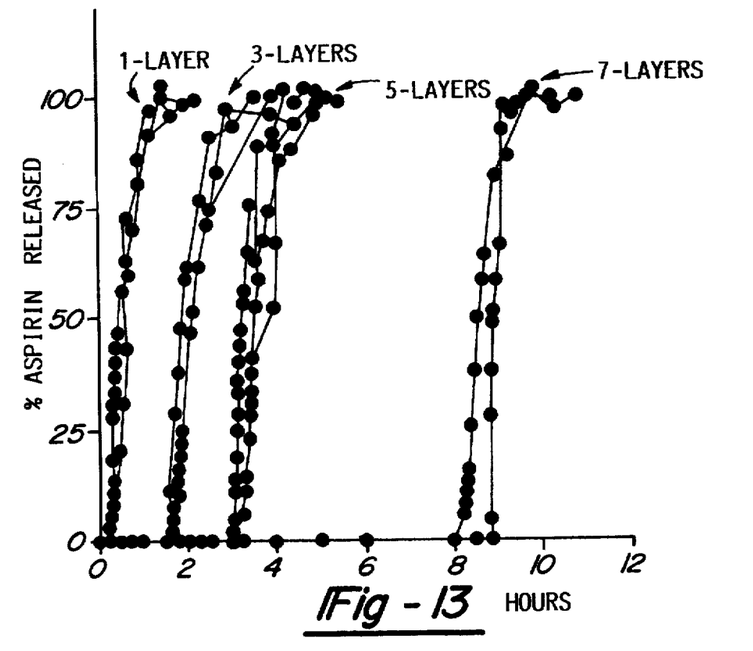
FIG. 13 is a graph showing the percent release of drug over time as a function of the number of coatings applied to capsules made in accordance with the present invention.

FIG. 13 illustrates the percent aspirin released over time as it correlates to the number of cellulose film coatings applied to the capsule subjected to Simulated Intestinal Fluid at pH 7.5 at 37° C.

Table V, FIG. 12, and FIG. 13 demonstrate that the length of release time increases as the number of layers or coatings of cellulose film coatings increased on the dosage form.

As shown in FIG. 4, there is absolutely no release from the capsules during the first 5 hours of testing. There was an immediate pulsatile release from the capsules beginning at five and six hours. Accordingly, capsules made in accordance with the present invention have the capacity to pulse release.

Several variables were evaluated with regard to the manufacturing techniques to determine their effect on pulse time. The results of these tests are shown in Table III.

As shown in Table III, plug variables such as the effect of the hydrophilic/lypophilic balance HLB of the plug on pulse time was tested. The HLB values were varied by varying the components used to make the plug. For example, different waxes have different HLB values. By combining different waxes, the HLB value of the resulting plug is varied. Specific examples are set forth in Table IV. Additionally, the temperature of the plug material, such as gelucire, prior to filling also effects pulse time.

Table III also shows the effect of coating variables such as spray rate, solids content and plasticizer content of the coating. What is also evident from Table III is that the variables tested were also effected by the percent coating, that is, the weight percent of the coating as compared to the weight of the remainder of the capsule.

Figure 5:
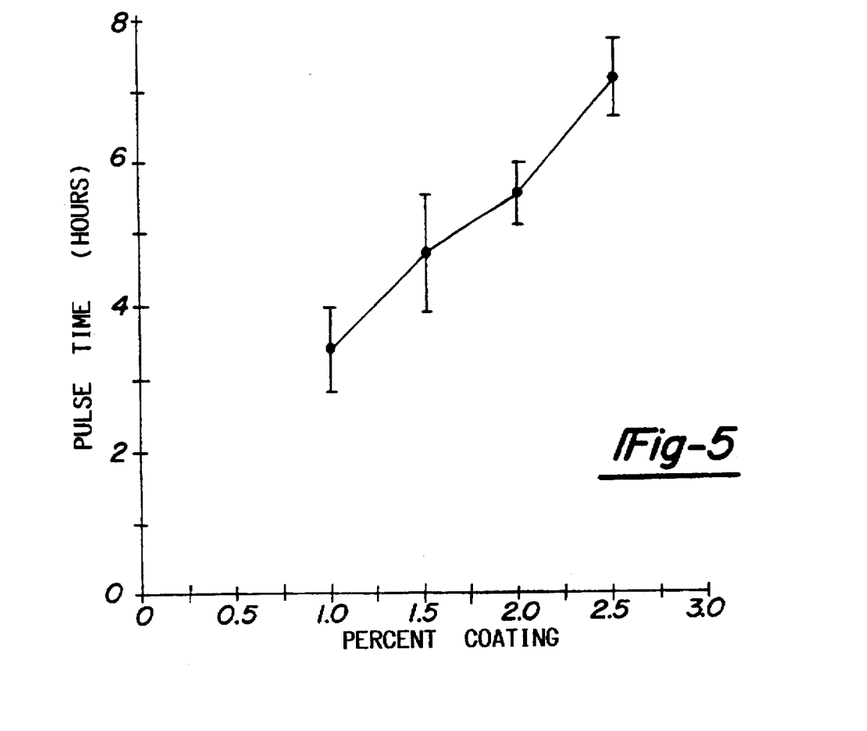
FIG. 5 is a graph showing the average pulse time as function of percent coating.

A more detailed analysis of the average pulse time as a function of percent coating is shown in FIG. 5. FIG. 5 shows an almost linear relationship between increased percent coating and pulse time. Thusly, one method of controlling the predetermined time of release is by changing the percent coating of the capsule. As in the prior experiments, this experiment was conducted by coating capsules as described above, determining their percent coating and the placing the capsules as batches based on their percent coating in 20 ml of buffer, 6.5 pH at 37° C. Captopril release was monitored by high pressure liquid chromatography.

Further studies were conducted on the effect of various osmotic agents as they effect water uptake within capsules. To perform these experiments, capsules as made above but filled with lactose, and lactose/sorbitol filled capsules were disposed in 20 ml of buffer, pH 6.5, at 37° C. Six of each capsule type were placed in buffer, the lactose filled capsules and the lactose/sorbitol filled capsules having either a 1.66 weight percent coating or 3.54 weight percent coating. After the periods of time indicated in FIGS. 6–8, the weight of the capsule was determined and percent weight gain was determined as showing comparative rates of the osmotic pressure gradients created by the various agents within the capsules.

Figure 6:
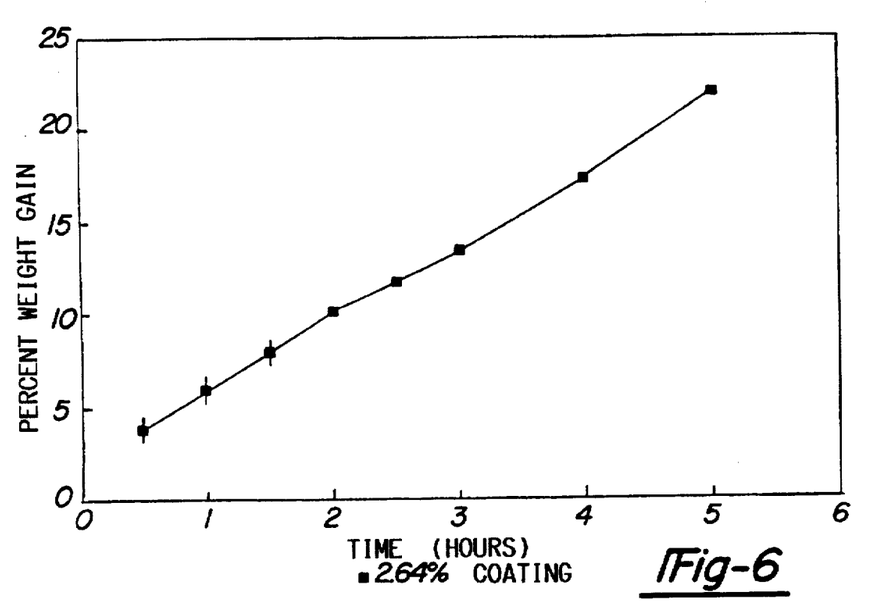
FIG. 6 shows graphically the results of water uptake studies on capsules made in accordance with the present invention showing percent weight gain over time.
Figure 7:
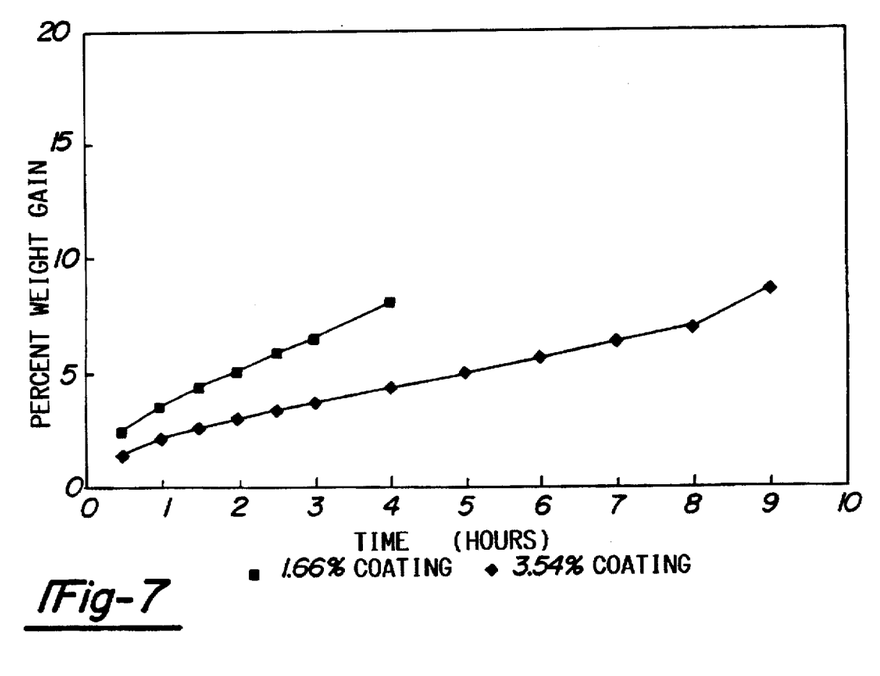
FIG. 7 shows the results of water uptake studies graphically on lactose filled capsules having different coating weights.
Figure 8:
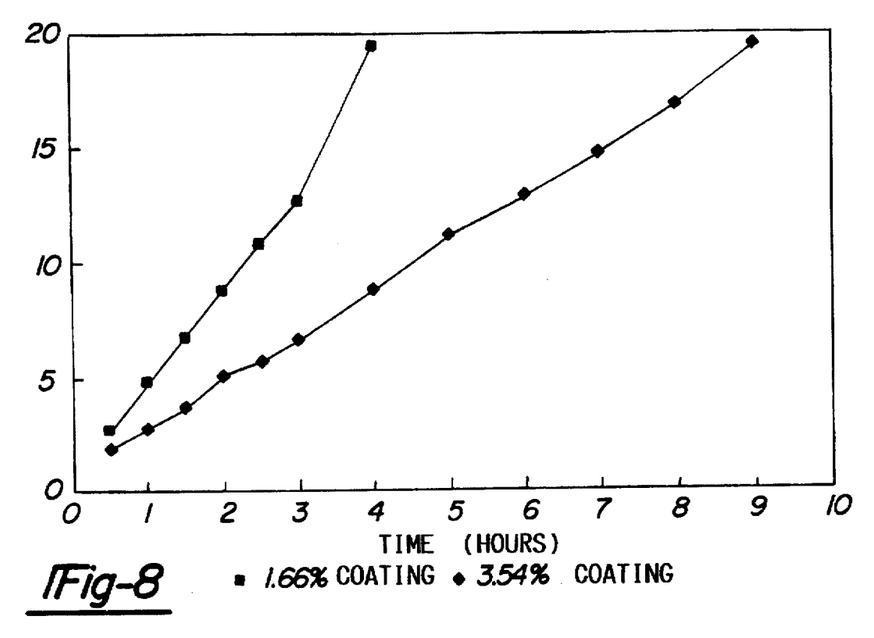
FIG. 8 shows the results of water uptake studies of capsules containing lactose/sorbitol therein, the capsules having two different weight coating thereon.

FIG. 6 shows an almost linear weight percent gain over time of the Captopril capsules, containing both lactose and sorbitol therein as discussed above. FIG. 7 shows a comparative decrease in weight percent gain over time in the capsules containing only lactose. The expected increase in rate is shown with capsules having the thinner coating of 1.66%. A similar phenomenon is shown with the lactose/sorbitol filled capsules, except that these capsules had a significant increase in rate compared to capsules containing lactose alone.

In view of the above data, the rate of the internal pressure gradient increase and the time period to release the plug member can be adjusted and controlled by adjusting the amount and type of osmotic agent within the capsules, as well as adjusting the thickness of the membrane coating.

Figure 3:
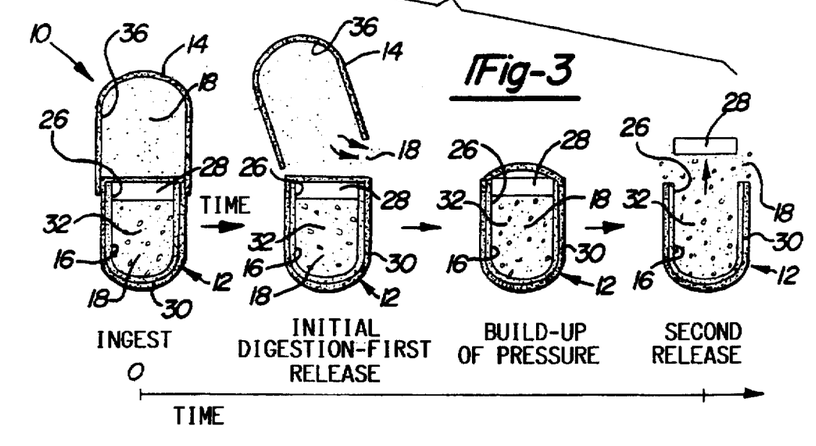
FIG. 3 schematically shows the steps of drug release from the drug delivery system of the present invention over time.

The present invention further provides a method of delivering a drug to a body, as schematically shown in FIG. 3. The steps generally include the ingestion of the drug delivery system 10 as shown in FIG. 3. FIG. 3 shows the delivery of the drug over a time, the time line being schematically shown at the bottom of the Figure. There is an initial release of the first predetermined amount of drug 18 from the first chamber 36 of the system 10 after ingestion. The first capsule half 12 remains intact within the membrane 30. As the first capsule half 12 travels through the digestive track it is exposed to the fluid therein, there is a pressure buildup within the inner chamber 16 of the system 10 over time. This forces the plug 28 from the passageway 26 at a predetermined time after the ingesting step. Finally, after the predetermined time, the plug 28 is completely forced from the passageway 26 thereby releasing the drug 18 from the inner chamber 16. A multichamber system works in the same manner with a later pulse of drug 18' being released from chamber 16' and plug 28' is forced out of the capsule half 12. As shown by the in vitro experiments above, the rate of osmotic pressure increase of the inner chamber 16 can be controlled by various variables such as the type and amount of osmotic agent as well as the thickness or percent coating of the membrane film 30.

Applicant has conducted bioavailability studies demonstrating the aforementioned method in vivo.

MATERIALS

Capsules, prepared as described above numbered from 3 to 7, were used for bioavailability study. Captopril tablets and powder for oral and intravenous studies were kindly donated by Squibb. Two male beagle dogs, weighing thirty-four and thirty pounds and two midgut-fistulated female dogs, weighing forty-seven and thirty-eight pounds respectively, were employed for the bioavailability studies. These dogs were fasted over fifteen hours before experiments were began.

Oral study—Four tablets containing 25 mg of Captopril were given to four dogs orally with 20 ml of tap water. Dogs were released from restraining sling for fifteen minutes four hours after the experiment was started for urination and a walk. Blood samples (1.2 ml) were collected through the forearm vein, which was catheterized with an 18G catheter (Abbott, Chicago, Ill.), at 0, 0.25, 0.5, 1, 1.5, 2, 2.5, 3, 3.5, 4, 5, and 6 hours and transferred to test tubes containing 5 mg of each N-ethylmaleimide (NEM) and ethylenediaminetetraacetic acid (EDTA) sodium and stored in a freezer until assay.

Intravenous study—50 mg of captopril powder was dissolved in 15 ml of saline and filtered through 0.22 μm sterilized filter paper right before the infusion was started. For each four dogs, this solution was infused over fifteen minutes into the catheterized forearm vein using a Harvard infusion pump. For this intravenous study, blood samples were collected from the other side of the forearm vein at 0, 1, 2, 3, 5, 8, 10, 13, 15, 16, 18, 20, 23, 25, 30, and 40 minutes and at 1, 2, 3, and 4 hours.

The study was duplicated in each dog. The experimental design was the same as the oral study except that the schedule for sample collection was every one hour for twelve to thirteen hours. Dogs were released from the sling every four hours for fifteen minutes.

GC-EC blood sample assay—All blood samples were assayed using gas chromatography with an electron-captured detector. The GC-EC assay, which was reported earlier by Bathala et al., was slightly modified and tested for linearity, precision, and accuracy. The standard curve was linear over the concentration range studied, with an r value of 0.9999. The detection limit based on a signal-to-noise ratio of 3 were 25 ng/ml. The determination of Captopril was highly reproducible, with a CV of less than 7% for all concentrations examined. The intra-and inter-day variability of the Captopril assay was not significant.

Materials—NEM, hexafluoro-2-propanol, trifluoroacetic anhydride, were reagent grade (Sigma Co., Mo.) and used as received. All other chemicals were reagent grade (Fisher Scientific, Chicago) or HPLC grade. Captopril and internal standard, SQ 25761, were obtained from E.R. Squibb & Sons (Princeton). The chromatographic column was capillary, 30 m×0.53 mm i.d. (1.2 mcl of film thickness), immobilized with 100% dimethyl polysiloxane (Cat. #19656, Alltech Assoc., Chicago Ill.). Nitrogen and argon-methane (95:5) of the highest available purity (Metro Welding Co., Detroit, Mich.), were used.

Equipment—Gas chromatography was preformed using HP 5890A (Hewlett Packard) gas chromatograph equipped with a nickel-63 electron-capture detector, 3393A HP integrator, 7673A HP controller, and 7673A HP automatic sampler. All extractions were carried out by shaking the samples on a Tekmar mixer (Janke & Kunkel Co., Funkentstort, West Germany). The N-Evap (Organomation Assoc., Northborough, Mass.) was used to remove benzene from extracts with a nitrogen stream. The esterification with hexafluoro-2-propanol were performed by incubating in a heating block (Lab-Line Instruments Inc., Melrose Park, Ill.).

Blood sample assay—After thawing blood samples by sonication, the blood was diluted with distilled water (1:1 by volume). An internal standard (615 ng/ml) was spiked into blood samples and excess NEM and naturally occurring interfering substances were removed by extraction with benzene followed by acidification and extracted with benzene and converted to their hexafluoroisopropyl esters. These were separated by GC-EC. Standard curves from spiked Captopril concentrations of 0.05, 0.5, 1, 10 mcg/ml in blood were prepared for daily working standards. For reproducibility studies, four concentrations for the standard curve were assayed in quadruplicate using the method described.

Data analysis—Area under curves (AUC) of time zero to t and time zero to infinity by extrapolating the last blood concentration with an elimination rate constant (ke) were evaluated from the oral, intravenous, and technology studies based on the noncompartmental analysis. Relative bioavailability of technology capsules were determined comparing to the oral study and normalized by the dose given.

In view of the experimental results, it can be concluded that capsules made in accordance with the present invention provide a pulsatile release of drugs effective in in vitro environments, as well as in vivo. Such a drug delivery system possess great potential for use in providing drugs to the public that have a first pass effect.

Figures 9A, 9B:
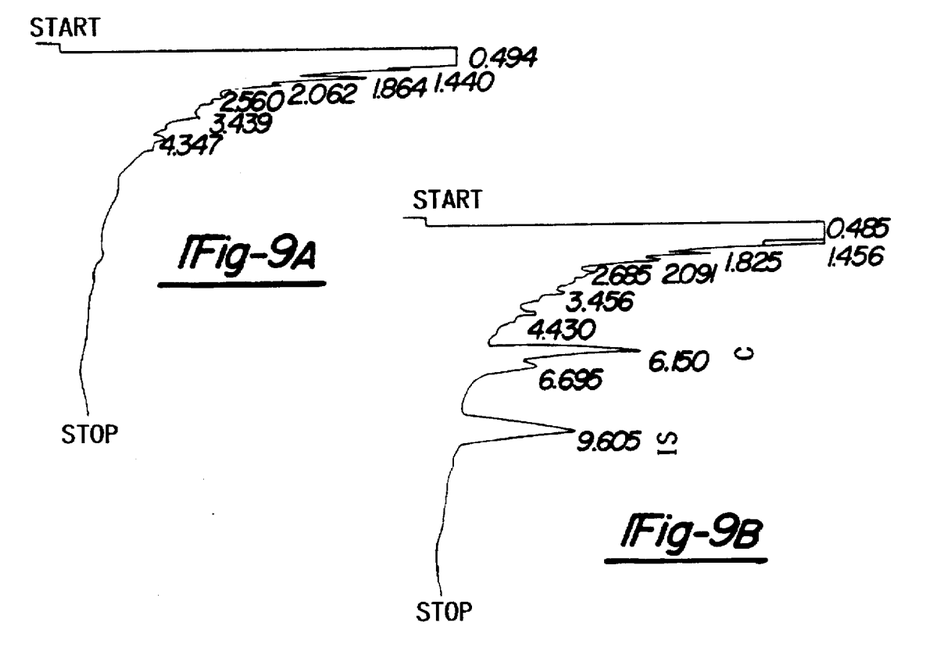

GC-EC assay described above with a slight modification using capillary column, was adequate for the present study. Typical chromatograms from blank blood samples and actual samples from dog studies are shown in FIGS. 9A and B respectively. The retention times of the derivatized captopril and internal standard were about 6.2 and 9.6 minutes, respectively. These retention times are different from those reported earlier by Bathala et al. This is probably due to the alteration in instrumentations. No interfering peaks were observed in the extracts of the blank dog blood. The derivatives of captopril and of internal standard were stable over one month (testing period) at room temperature.

Figure 10:
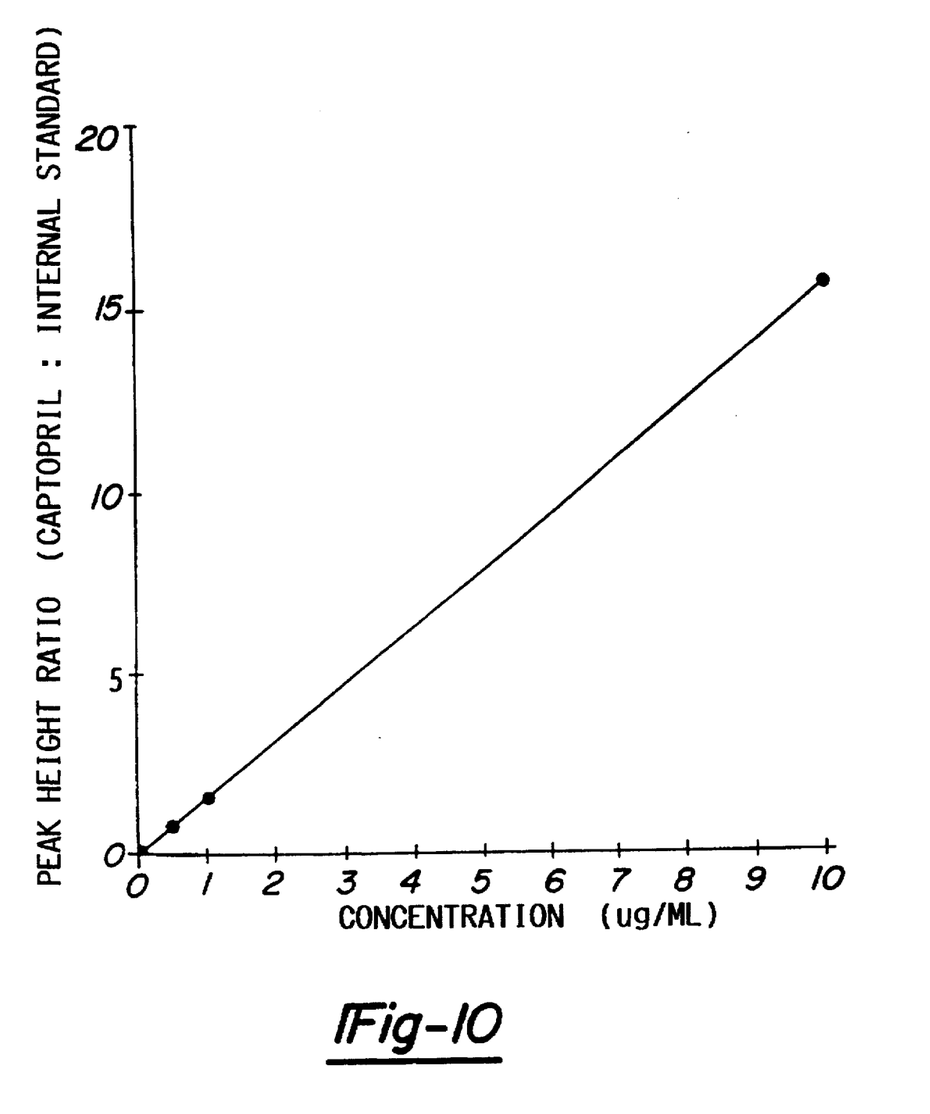
FIG. 10 shows a plot of chromatographic peak height ratio versus concentration.

A plot of chromatographic peak height ratio versus concentration was linear for captopril from 0.05 to 1 mcg/ml (FIG. 10). The correlation coefficient and the y-intercept for the straight lines were 0.999 and 0.003, respectively. The average coefficient of variation (CV) for all the concentrations examined was +7%. The linearity and reproducibility of the GC-EC method in dog blood by Bathala et al., was demonstrated by 4 consecutive calibration curves in FIG. 2.

Figure 11A:
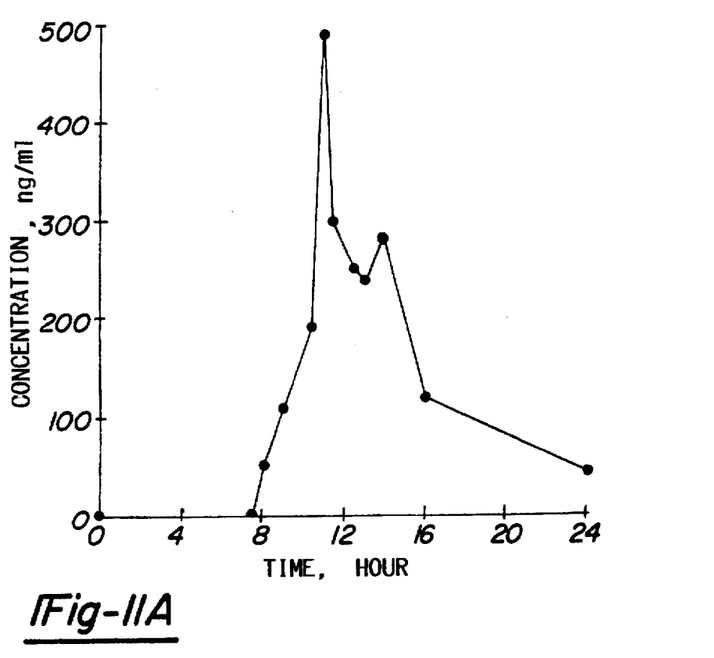
FIGS. 11A and B show two graphs illustrating the pulsatile release of drug in vivo.
Figure 11B:
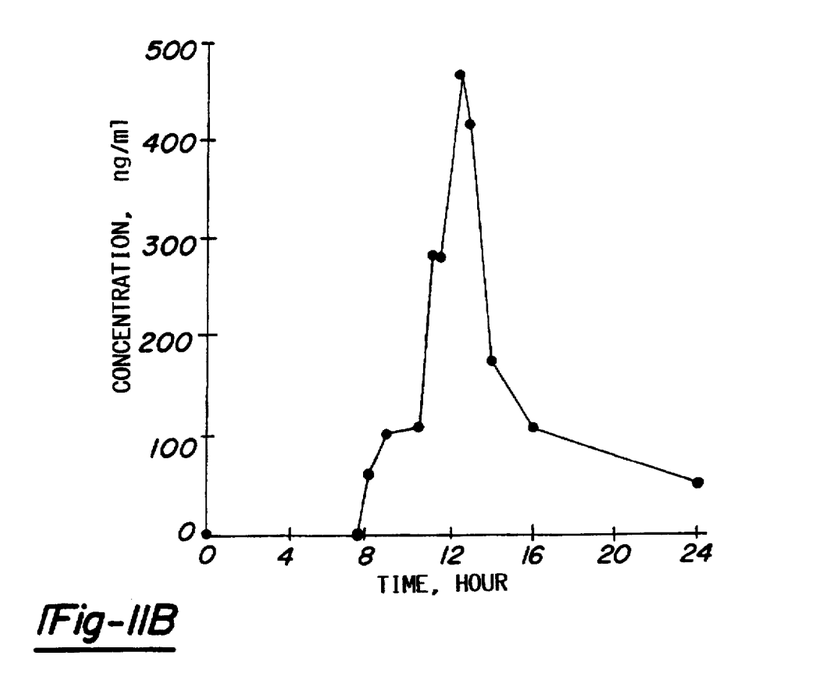

FIGS. 11A and 11B show the results of two dog studies wherein capsules made in accordance with the present invention were ingested. The capsules contained captopril and were made as discussed above. Blood samples were analyzed at the times indicated. There was no release of drug prior to the eight hour time point followed by a pulse or peak of drug. The pulse was a well defined peak. Accordingly, the present invention has been shown to function in vitro as well as in vivo.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

TABLE I

| 66 DRUGS WHICH HAVE A FIRST-PASS EFFECT |
| --- |
| ALDOSTERONE |
| ALPRENOLOL |
| AMITRYPTYLINE |
| ASPIRIN |
| BECLOMETHASONE DIPROPIONATE |
| BROMOCRIPTINE MESYLATE (F ≈ 0.06) |
| BUTORPHANOL TARTRATE |
| CHLORPROMAZINE HCL |
| CIMETIDINE (F ≈ 0.7) |
| CODEINE |
| CORTISONE |
| CYCLOBENZAMINE HCL |
| DESMETHYLIMIPRAMINE |

TABLE I-continued

66 DRUGS WHICH HAVE A FIRST-PASS EFFECT

DIHYDROERGOTAMINE MESYLATE
DILTIAZEM HCL
DOBUTAMINE HCL
DOPAMINE HCL
EPINEPHRINE
ERGOLOID MESYLATES
ERGOTAMINE TARTRATE
ESTRADIOL
ETHINYLESTRADIOL (F ≃ 0.4)
FLUNISOLIDE
FLUOROURACIL
5-FLUORO-21-DEOXYURIDINE
GUANETHIDINE SULFATE
HYDRALAZINE HCL
IMIPRAMINE HCL
ISOETHORINE HCL & MESYLATE
ISOPROTERENOL SULFATE
ISOSORBIDE DINITRATE
LEVALLORPHAN TARTRATE
LIDOCAINE HCL
MEPERIDINE HCL
6-MERCAPTOPURINE
METAPROTERENOL SULFATE
METHOXAMINE HCL
METHYLPREDNISOLONE (F ≃ 0.85)
METHYLTESTOSTERONE
METOPROLOL TARTRATE
MORPHINE SULFATE
NALBUPHINE HCL
NALOXONE HCL
NEOSTIGMINE
NIFEDIPINE
NITROGLYCERIN
NOREPINEPHRINE BITARTRATE
NORETHINDRONE (F ≃ 0.65)
NORTRIPTYLENE HCL
OXPRENOLOL
OXYPHENBUTAZONE
PENICILLAMINE
PENTAZONCINE HCL & LACTATE
PHENACETIN
PHENTOLAMINE HCL & MESYLATE
PHENYLEPHRINE HCL & BITARTRATE
PREDNISONE (F ≃ 0.85)
PROGESTERONE
PROPOXYPHENE HCL & NAPSYLATE
PROPRANOLOL HCL
RITODRINE HCL
SALICYLAMIDE
SALBUTAMOL
TESTOSTERONE
TIMOLOL MALEATE
VERAPAMIL HCL

SOURCE OF INFORMATION WAS DRUG INFORMATION 84, AMERICAN HOSPITAL FORMULARY SERVICE, AMERICAN SOCIETY OF HOSPITAL PHARMACISTS.

TABLE II

| | |
|---|---|
| Captopril, USP* | 67.00 |
| Citric Acid, Anhydrous, USP | 100.00 |
| Lactose, Anhydrous, USP | 41.00 |
| Microcrystalline Cellulose, NF | 97.35 |
| Sorbitol, NF | 35.00 |
| Croscarmellose Sodium, NF | 7.00 |
| Magnesium Stearate, BP | 1.75 |
| Gelocire 50/02 | 120.00 |
| Size #0 hard gelatin two piece capsules Captopril immediate release blend (50%) Coating solution for captopril pulsatile release capsules q.s. to obtain suitable release | 66.00 |

*Microcrystalline cellulose weight to be adjusted based on captopril, USP potency.

TABLE III

Pulsatile Delivery System - variable evaluation:

| Variable | % Coat | Pulse Time | n |
|---|---|---|---|
| Plug Variables: | | | |
| Hydrophilic/Lipophilic Balance (HLB of The Gelucire) | | | |
| 5.5 | 2.80% | 5.00 | 16 |
| 4.0 | 2.75% | 3.95 | 33 |
| 2.0 (current formula) | 2.82% | 6.07 | 12 |
| Temperature of the Gelucire prior to filling | | | |
| 85 C. | 2.78% | 6.52 | 17 |
| 75 C. | 2.82% | 6.07 | 12 |
| 60 C. (current procedure) | 2.85% | 3.42 | 24 |
| Coating Variables: | | | |
| Spray Rate | | | |
| Slow (0.038%/appln. | 3.02% | 3.15 | 48 |
| Fast (0.12%/appln. | 2.93% | 4.43 | 43 |
| (Current appln. rate is 0.080%) | | | |
| Solids Content (C. acetate, C. acetate butyrate) | | | |
| 2.8% | 1.0% | 1.07 | 6 |
| | 1.8% | 2.65 | 6 |
| | 2.6% | 3.66 | 6 |
| (Current formula has a 4.2% solids content) | | | |
| Plasticizer | 1.11% | 1.71 | 6 |
| 4% PEG 200 | 1.91% | 3.47 | 6 |
| 0% PEG 200 | 1.13% | 3.01 | 5 |
| (current formula) | 1.46% | 5.04 | 7 |

TABLE IV

Examples of mixtures of plug materials to control HLB value

| | Plug Material | HLB |
|---|---|---|
| 1. | Partial glycerides and PEG fatty esters | 10 |
| 2. | Partial glycerides and PEG fatty esters | 6 |
| 3. | Glyceryl stearate | 2 |
| 4. | Glyceryl palmitostearate | 2 |

Mixtures of the above materials can be mixed together to achieve Plug materials of varying HLB values.

| | | |
|---|---|---|
| 5. | 50% Partial glycerides and PEG fatty esters (HLB 10) and 50% Glyceryl sterate | 6 |
| 6. | 50% Partial glycerides and PEG fatty esters (HLB 6) and 50% Glyceryl palmitostearate | 4 |

Release Results

| # of coats applied | % w/w of coat applied | Release Times (hours) |
|---|---|---|
| 1 | 0.18 | 0.23 ± 0.03 |
| 3 | 0.81 | 1.68 ± 0.04 |
| 5 | 1.85 | 2.96 ± 0.31 |
| 7 | 2.90 | 8.53 ± 0.28 |

What is claimed is:

1. A method of making a drug delivery capsule (10) consisting essentially of the sequential steps of: (a) filling a first capsule half with a drug and an osmotic agent, the capsule being water permeable; (b) plugging an open-end (24) of the capsule (12) with a plug being selected from the group consisting of fatty acids and esters thereof, waxes, polyethylene glycol, polyglycolyzed glycerides, and mixtures thereof; (c) disposing a water permeable cellulose film (30) over the capsule (12) and plug (28) wherein when the capsule half (12) is spray coated, the concentration of the coating material ranges from about one to ten percent (w/v) of solvent; (d) filling a second capsule half (14) with a drug (18); (e) releasably mounting an open-end (34) of the second capsule half (14) over the plugged end (24) of the first capsule half (12); and (f) cursing the coated capsule wherein when the capsule half (12) is dip coated, the capsule half (12) is cured at a temperature range from about 20° C.–60° C. for a time period from about one minute to 24 hours.

2. A method as set forth in claim 1 wherein said disposing step is further defined as dipping the capsule and plug in a container containing the water permeable film at a temperature range of about 15°–40° C. in order to apply a coating of film over the capsule and plug and curing the coated capsule.

3. A method as set forth in claim 1 wherein said disposing step is further defined as spraying a coating of the film over the capsule and plug.

4. A method as set forth in claim 1 wherein the capsule is coated prior to said filling step.

5. A method as set forth in claim 1, wherein the fatty acid esters include glyceryl palmitostearate, glyceryl stearate, polyethylene glycol fatty acid esters, and mixtures thereof.

* * * * *